(12) United States Patent
Richardson et al.

(10) Patent No.: US 6,416,752 B1
(45) Date of Patent: Jul. 9, 2002

(54) TERMITE BAIT COMPOSITION AND METHOD

(75) Inventors: Ronald O. Richardson, Ellisville; Robin L. Kern, Fenton, both of MO (US)

(73) Assignee: Whitmire Micro-Gen Research Laboratories, Inc., St. Louis, MO (US)

(*) Notice: Subject to any disclaimer, the term of this patent is extended or adjusted under 35 U.S.C. 154(b) by 0 days.

(21) Appl. No.: 09/754,722

(22) Filed: Jan. 4, 2001

(51) Int. Cl.⁷ .................. A01N 25/12; A01N 25/00; A01N 43/04; A01N 43/88; A01N 59/14
(52) U.S. Cl. .................. 424/84; 424/405; 424/409; 424/411; 424/412; 424/413; 424/414; 424/416; 424/417; 424/418; 424/489; 424/490; 424/494; 424/657; 424/658; 424/659; 424/660; 424/682; 424/DIG. 11; 514/28; 514/30; 514/57; 514/64; 514/183; 514/229.2; 514/341; 514/345; 514/406; 514/407; 514/450; 514/453; 514/549; 514/594; 514/951; 43/131
(58) Field of Search .................. 424/84, 405, 409, 424/489, 490, 494, DIG. 11, 411–414, 416–418, 657–660, 682; 514/951, 28, 30, 57, 64, 183, 229.2, 341, 345, 406, 407, 450, 453, 549, 594; 43/131

(56) References Cited

U.S. PATENT DOCUMENTS

| | | |
|---|---|---|
| 4,363,798 A | 12/1982 | D'Orazio |
| 5,303,502 A | 4/1994 | Metzner et al. |
| 5,359,806 A | 11/1994 | Jeffery et al. |
| 5,609,879 A | 3/1997 | Myles |
| 5,678,362 A | 10/1997 | Hulls et al. |
| 5,741,524 A | * 4/1998 | Staniforth et al. .......... 424/489 |
| 5,802,779 A | 9/1998 | Hulls et al. |
| 5,820,855 A | 10/1998 | Barcay et al. |
| 5,937,571 A | 8/1999 | Megargle |
| 5,960,584 A | 10/1999 | Aesch, Jr. |
| 6,065,241 A | 5/2000 | Woodruff |
| 6,079,150 A | 6/2000 | Setikas et al. |
| 6,088,950 A | 7/2000 | Jones |
| 6,094,857 A | 8/2000 | Kennedy et al. |

FOREIGN PATENT DOCUMENTS

| | | | |
|---|---|---|---|
| JP | 2000-7516 | * | 1/2000 |
| NL | 7608806 | * | 2/1977 |
| WO | WO 99/18789 | | 4/1999 |

OTHER PUBLICATIONS

Derwent Abstract 1977–14040Y, abstracting NL7608806, 1977.*
CROPU Abstract 2000–88930, abstracting JP2000–7516, Jan. 2000.*
Derwent Abstract 1981–64579D, abstracting GB159 7293, 1981.*
Derwent Abstract 1989–304343, abstracting JP01–224307, 1989.*

* cited by examiner

Primary Examiner—John Pak
(74) Attorney, Agent, or Firm—Senniger, Powers, Leavitt & Roedel

(57) ABSTRACT

An improved termite bait composition comprises a powdered cellulosic attractant having a particle size in the range of approximately 1 to 100 micrometers and a termite killing agent. Also disclosed are a method for controlling termites by applying the termite bait composition to a termite infested area and a termite bait composition package for use in a termite bait station comprising the termite bait composition contained within a termite attractive package.

18 Claims, No Drawings

TERMITE BAIT COMPOSITION AND METHOD

BACKGROUND OF THE INVENTION

This invention relates to termite bait compositions and methods for controlling termites and, more particularly, to such compositions and methods which employ a powdered cellulosic attractant having a particle size in the range of approximately 1 to 100 micrometers.

In the prior art, the use of chemical attractants and feeding stimulants have been known to enhance the efficacy of insect or termite bait compositions by increasing the attraction to or increasing the ingestion rate of insect or termite baits. Thus, the prior art teaches the use of bait attractants comprised of paper, wood or other cellulose derived materials and such bait attractants have assumed the physical form of wooden blocks, saw dust, shredded paper or cardboard. The active termite killing agent or ingredient is generally incorporated into such baits by known methods such as absorption, blending or other conventional formulating means. Reference is made to U.S. Pat. Nos. 4,363,798, 5,609,879, 5,802,779, 5,820,855 and 5,937,571 for disclosures relating to prior art termite bait compositions and methods for controlling termites. The prior art is devoid of any mention of the use of attractants of a particle size less than 100 micrometers.

SUMMARY OF THE INVENTION

Among the several objects of the invention may be noted the provision of a termite bait composition and method for controlling termites in which a powdered cellulosic dust having a particle size in the range of 1 to 100 micrometers is employed as an attractant; the provision of such a termite bait composition and method in which the use of such a cellulosic attractant promotes increased ingestion and consequent exposure of termites to termite controlling or killing agents; the provision of such a termite bait composition and method in which such a cellulosic attractant permits better adherence of the composition to termites thereby increasing the prospects for introduction of the termite controlling or killing agent back to the termite colony by contact and grooming; and the provision of such a termite bait composition and method which may be readily and economically practiced for improved control of termites. Other objects will be in part apparent and in part pointed out hereinafter.

Briefly, the present invention is directed to a termite bait composition comprising a powdered cellulosic attractant having a particle size in the range of approximately 1 to 100 micrometers and a termite killing agent carried by or within the attractant. The invention is also directed to a method for controlling termites which comprises applying to a termite infested area the above-noted termite bait composition. The invention is further directed to a termite bait composition package for use in a termite bait station comprising the above-noted termite bait composition contained within a closed cellulosic package.

DESCRIPTION OF THE PREFERRED EMBODIMENTS

In accordance with the present invention, it has now been found that an improved termite bait composition is provided by utilizing as an attractant a powdered cellulosic material having a particle size in the range of approximately 1 to 100 micrometers with a termite killing or controlling agent being carried by or within the attractant. By using powdered cellulosic material of this small particle size as an attractant, it has been found that the resulting termite bait composition leads to increased ingestion since the termites may more easily ingest material of this small particle size. The fine particle size of the termite bait composition of the invention also improves physical exposure by better adhering to termite bodies through static electrical charge. Thus, the fine powdered bait composition containing the termiticide or killing agent more readily adheres to the termites and is carried back to the nest where it becomes distributed throughout the colony by contact and grooming. The bait composition and method of the present invention thereby lead to improved control of termite colonies through the increased ingestion by termites and better adherence to termites of the bait composition by reason of the employment of powdered cellulosic material of small particle size as an attractant.

For use as the attractant in the practice of the invention, any cellulosic material having a particle size within the range of approximately 1 to 100 micrometers may be employed. The dust or powdered attractant of this particle size may be cellulose, microcrystalline cellulose, paper or mixtures thereof. The preferred cellulosic material for use as the attractant in the present invention is microcrystalline cellulose such as that marketed under the trade designation "Lattice NT-020 Microcrystalline cellulose" having an average particle size of 20 micrometers (FMC Corporation). It will be understood that other cellulosic materials having a particle size within the range of approximately 1 to 100 micrometers, preferably 20 to 100 micrometers and more preferably 20 to 50 micrometers, may also be used in the practice of the invention.

Any known termite killing or controlling agent or termiticide can also be used in the practice of the invention. These include chitin synthesis inhibitors such as hexaflumuron, flufenoxuron, lufenuron and dimilin, juvenile hormone mimics such as methoprene and pyriproxyfen, stomach toxicants such as sulfuramide, abamectin, cryolite, boric acid and alkali and alkaline earth salts of boric acid, and contact insecticides such as thiamethoxam, imidacloprid and fipronil, or mixtures or combinations of these agents. The particle size of the termite killing agent employed may vary over a wide range, but is preferably of the same order as the particle size of the cellulosic attractant discussed above. The use of dimilin as the termite killing agent is preferred and the highly preferred particle size range for dimilin is approximately 2 to 5 micrometers. The termite killing or controlling agent may be present in the bait composition in various concentrations such as 0.1 to 1% by weight.

In preparing the termite bait compositions of the invention, the termite killing agent or termiticide utilized is generally incorporated into the particular cellulosic attractant employed by absorption, blending or other conventional formulating means. As thus prepared, the termite killing agent is carried by or within the cellulosic attractant.

In another embodiment of the invention, the termite bait composition may be compressed into tablets or granular form for placement in a termite bait station.

In a further embodiment of the invention, the termite bait composition of the invention prepared as described above is packaged in a termite attractive package such as a paper bag, cardboard tube or other cellulosic container which may then be dropped into or placed in a termite bait station without being opened. In this embodiment, termites eat through the cellulosic package material and thereby gain access to the bait composition contained therein. The use of the package for the bait composition enables the powdered bait composition to be maintained in a fresh condition until it is used and also renders handling of the packaged bait composition safer since the user is not required to come into direct contact with the killing agent or toxicant in the packaged bait composition.

The following examples illustrate the practice of the invention.

EXAMPLE 1

The following formulations were tested to determine their relative efficacy as termite bait attractants:

| Formulation No. | Formulation |
|---|---|
| 017 | Portabella mushrooms/microcrystalline cellulose |
| 018 | Button mushrooms/microcrystalline cellulose |
| 019 | Shittake mushrooms/microcrystalline cellulose |
| 020 | Button mushrooms/microcrystalline cellulose/powdered chicken fat |

-continued

| Formulation No. | Formulation |
|---|---|
| 022 | Portabella mushrooms |
| 023 | Button mushrooms |
| 024 | Shittake mushrooms |
| 025 | Microcrystalline cellulose |
| 053 | Microcrystalline cellulose/powdered chicken fat |
| 054 | Solka Flock (chopped up noncrystallized cellulose) |
| Wood control | Pine wood |

The microcrystalline cellulose used had an average particle size of 20 micrometers and the Solka Flock used had an average particle size in the range of 20 to 100 micrometers.

The tests were conducted using a choice test arena arrangement in which eight feeding chambers surround a central termite chamber in a wheel configuration with tubes extending from the central chamber to each of the feeding chambers or bait stations. One feeding chamber was left empty for these 7-way tests. There were three combinations of the 11 termite bait attractants presented simultaneously to a group of termites (*Reticulitermes flavipes* (Kollar)). Each combination included pine wood as one choice (the control or standard food) and only one bait (054) was presented in each of the three combinations. There were four replicates of each combination of bait attractants.

The following table summarizes the results of the tests in terms of termite feeding rates (mg of bait removed/g of termite/day).

| | FEEDING RATE | | | | | | |
|---|---|---|---|---|---|---|---|
| | BAIT TYPE/NUMBER | | | | | | |
| Replicate | 17 | 19 | 22 | 24 | 25 | 54 | wood |
| 1) | 7.73 | 14.28 | 10.34 | 15.35 | 13.87 | 9.94 | 5.67 |
| 2) | 13.52 | 24.60 | 15.03 | 6.27 | 10.43 | 9.15 | 5.04 |
| 3) | 21.94 | 22.22 | 16.28 | 11.04 | 21.94 | 8.85 | 4.75 |
| 4) | 1.89 | 4.71 | 13.40 | 7.00 | 15.22 | 13.34 | 1.14 |
| mean ± se | 11.27± 8.5 | 16.45± 8.9 | 13.76± 2.6 | 9.92± 4.2 | 15.37± 4.8 | 9.82± 2.7 | 4.15± 2.0 |
| | BAIT TYPE/NUMBER | | | | | | |
| Replicate | 20 | 22 | 23 | 24 | 25 | 54 | wood |
| 1) | 3.21 | 1.76 | 0.00 | 19.39 | 0.00 | 0.96 | 14.41 |
| 2) | 11.74 | 13.34 | 4.72 | 15.70 | 13.47 | 10.78 | 2.49 |
| 3) | 5.96 | 21.82 | 5.11 | 18.57 | 17.96 | 12.85 | 5.03 |
| 4) | 6.79 | 10.30 | 2.70 | 13.89 | 17.47 | 11.49 | 0.06 |
| mean ± se | 6.93± 3.6 | 11.81± 8.3 | 3.13± 2.3 | 16.88± 2.5 | 12.22± 8.4 | 9.02± 5.4 | 5.50± 6.3 |
| | BAIT TYPE/NUMBER | | | | | | |
| Replicate | 18 | 20 | 23 | 53 | 54 | wood | |
| 1) | 8.27 | 7.95 | 0.98 | 8.80 | 7.55 | 4.53 | |
| 2) | 13.27 | 8.35 | 0.00 | 5.21 | 6.66 | 2.02 | |
| 3) | 13.36 | 8.08 | 0.00 | 19.40 | 9.49 | 3.30 | |
| 4) | 11.76 | 6.95 | 0.00 | 19.04 | 11.37 | 4.74 | |
| mean ± se | 11.66± 2.4 | 7.83± 0.6 | 0.25± 0.49 | 13.11± 7.2 | 8.77± 2.1 | 3.65± 1.3 | |

The following table shows the average of the mean feeding rates (mg of bait/g of termite/day) for the above-noted tests.

|             | Average of Means mg/g/day |        |        |
| ----------- | ------ | ------ | ------ |
| Formulation | Mean 1 | Mean 2 | Mean 3 |
| 017         | 11.27  |        |        |
| 018         | 11.66  |        |        |
| 019         | 16.45  |        |        |
| 020         | 7.38   | 6.93   | 7.83   |
| 022         | 12.79  | 13.76  | 11.81  |
| 023         | 1.69   | 3.13   | 0.25   |
| 024         | 13.4   | 9.92   | 16.88  |
| 025         | 13.80  | 15.37  | 12.22  |
| 053         | 13.11  |        |        |
| 054         | 9.20   | 9.82   | 9.02   |
| Wood control| 4.43   | 4.15   | 5.5    |

As shown, microcrystalline cellulose (formulation 025) is an effective termite bait attractant.

EXAMPLE 2

The termite bait active ingredients or killing agents diflubenzuron, emamectin benzoate and thiamethoxam were tested for their efficacy. The termite species tested was *Reticulitermes virginicus*. The methodology employed was the standard "choice box" test used in Example 1 in which termites were released into a central chamber with untreated wood. The central chamber was connected, using Tygon tubing (2 mm I D), with peripheral feeding chambers containing a termite bait composition of the invention (microcrystalline cellulose powder having an average particle size of 20 micrometers and a termite killing agent) or untreated pine wood. Each replicate was given the choice of one gram of the treated cellulose powder or three blocks (1 cm) of untreated pine wood. At the end of 25 or 37 days, the number of live termites was counted. At the same time, the amount of pine wood or termite bait composition consumed was measured. The treatments were replicated two times.

| Treatment | Days in Bioassay | Percent Survivorship | Amount of Cellulose Powder Removed | Amount of Wood Removed |
| --- | --- | --- | --- | --- |
| Thiamethoxam 0.05% | 25 | 0 | 0.01 g | 0 |
| Thiamethoxam 0.05% | 25 | 0 | 0.01 g | 0 |
| Emamectin 0.05% | 25 | 0 | 0.13 g | 0 |
| Emamectin 0.05% | 25 | 0 | 0.07 g | 0 |
| Dimilin 0.5% | 37 | 0.1% | 0.33 g | 0.39g |
| Dimilin 0.5% | 37 | 0 | 0.06 g | 0.18g |
| Control | 37 | 89% | 0.84 g | 1.26g |
| Control | 37 | 99% | 0.82 g | 1.38g |

As can be seen, the bait compositions containing thiamethoxam and emamectin benzoate killed termites by contact whereas dimilin killed termites by ingestion. The results show that dimilin gave almost complete control after 37 days exposure and thiamethoxam and emamectin benzoate both killed 100% of the termites after 25 days. Relatively little cellulose powder was consumed but more treated powder was removed than was untreated wood.

In view of the above, it will be seen that the several objects of the invention are achieved and other advantageous results attained.

As various changes could be made in the above methods and compositions without departing from the scope of the invention, it is intended that all matter contained in the above description and shown in the accompanying drawings shall be interpreted as illustrative and not in a limiting sense.

What is claimed is:

1. A termite bait composition comprising a powdered microcrystalline cellulose attractant having a particle size in the range of approximately 1 to 100 micrometers and a termite killing agent.

2. A termite bait composition as set forth in claim 1 wherein said termite killing agent is selected from the group consisting of chitin synthesis inhibitors, juvenile hormone mimics, stomach toxicants, contact insecticides and mixtures thereof.

3. A termite bait composition as set forth in claim 1 wherein said powdered microcrystalline cellulose attractant has a particle size in the range of approximately 20 to 50 micrometers.

4. A termite bait composition as set forth in claim 1 wherein said chitin synthesis inhibitor is selected from the group consisting of hexaflumuron, flufenoxuron, lufenuron and dimilin.

5. A termite bait composition as set forth in claim 1 wherein said juvenile hormone mimic is selected from the group consisting of methoprene and pyriproxyfen.

6. A termite bait composition as set forth in claim 1 wherein said stomach toxicant is selected from the group consisting of sulfuramide, abamectin, cryolite, boric acid and alkali and alkaline earth salts of boric acid.

7. A termite bait composition as set forth in claim 1 wherein said contact insecticide is selected from the group consisting of thiamethoxam, imidacloprid and fipronil.

8. A method for controlling termites which comprises applying to a termite infested area a termite bait composition comprising a powdered microcrystalline cellulose attractant having a particle size in the range of approximately 1 to 100 micrometers and a termite killing agent.

9. A method for controlling termites as set forth in claim 8 wherein said termite killing agent selected from the group consisting of chitin synthesis inhibitors, juvenile hormone mimics, stomach toxicants, contact insecticides or mixtures thereof.

10. A method for controlling termites as set forth in claim 9 wherein said powdered microcrystalline cellulose attractant has a particle size in the range of approximately 20 to 50 micrometers.

11. A method for controlling termites as set forth in claim 9 wherein said synthesis inhibitor is selected from the group consisting of hexaflumuron, flufenoxuron, lufenuron and dimilin.

12. A method for controlling termites as set forth in claim 9 wherein said juvenile hormone mimic is selected from the group consisting of methoprene and pyriproxyfen.

13. A method for controlling termites as set forth in claim 9 wherein said stomach toxicant is selected from the group consisting of sulfuramide, abamectin, cryolite, boric acid and alkali and alkaline earth salts of boric acid.

14. A method for controlling termites as set forth in claim 9 wherein said contact insecticide is selected from the group consisting of thiamethoxam, imidacloprid and fipronil.

15. A termite bait composition package for use in a termite bait station comprising a termite bait composition containing a powdered microcrystalline cellulose attractant having a particle size in the range of approximately 1 to 100 micrometers and a termite killing agent, said composition being contained within a termite attractive package.

16. A termite bait composition package as set forth in claim 15 wherein said termite attractive package is composed of a cellulosic material.

17. A termite bait composition package as set forth in claim 16 wherein said cellulosic material is paper.

18. A termite bait composition package as set forth in claim 15 wherein said powdered microcrystalline cellulose attractant has a particle size in the range of approximately 20 to 50 micrometers.

* * * * *